United States Patent [19]

Mahler

[11] 4,038,986
[45] Aug. 2, 1977

[54] DERMATOME

[76] Inventor: Dan E. Mahler, 16 Hakneset Hagdulla, Tel Aviv, Israel

[21] Appl. No.: 624,830

[22] Filed: Oct. 22, 1975

[51] Int. Cl.² .................. A61B 17/322; B26B 3/00
[52] U.S. Cl. ................... 128/305.5; 30/280; 30/283
[58] Field of Search ............ 30/123.5, 278, 280, 30/283; 128/305.5

[56] References Cited

U.S. PATENT DOCUMENTS

| 3,428,045 | 2/1969 | Kratzsch et al. | 128/305.5 |
| 3,670,734 | 6/1972 | Hardy, Jr. | 128/305.5 |
| 3,820,543 | 6/1974 | Vanjushin et al. | 128/305.5 |
| 3,934,591 | 1/1976 | Gleason | 128/305.5 |

Primary Examiner—Channing L. Pace
Attorney, Agent, or Firm—Friedman, Goodman & Teitelbaum

[57] ABSTRACT

A dermatome for cutting thin organic tissue sections for transplanting, the dermatome comprising a thin resilient cutting band provided with a cutting surface disposed along a longitudinal edge of the cutting band. A T-shaped support member positions the cutting surface of the cutting band relative to the tissue sections. The head portion of the support member holds portions of the cutting band to determine the width of the cut tissue sections, the cutting band being held in a loop-like arrangement with the cutting surface extending along a bight portion thereof. The head portion of the support member also includes a guide element for determining the depth or thickness of the cut tissue sections, the guide element being disposed between the spaced apart cutting band portions and being spaced a preselected distance from the bight portion. Attachment elements are provided on the support member to permit connection of the support member to a handle member. The cutting band may be removably connected to the support member, or the cutting band may be integrally secured to the support member in a non-removable arrangement.

6 Claims, 6 Drawing Figures

DERMATOME

BACKGROUND OF THE INVENTION

The present invention relates generally to a dermatome, and more particularly to a dermatome for cutting thin organic tissue sections for transplanting, such as in gingival surgical grafts.

The present approach in gingival surgical grafts, is for the surgeon to transplant tissue from the patient's pallet to the gum area requiring the graft, such in the case of receding gums. This transplant is usually performed by the surgeon using a scapel to cut the tissue from the pallet, then placing the cut tissue on the gum and holding the tissue in place by conventional stitching until the tissue adheres to the gum. The thickness of the graft is important, and for best results, should be from 0.75 to 1.25 mm. If the graft is too thick, it will not adhere properly to the gum. If the graft is too thin, it will not hold. Accordingly, in the prior art, the thickness of the graft is entirely dependent upon the skill of the surgeon. Additionally, the thickness of the graft affects the healing of the pallet from which it is cut and therefore, the comfort of the patient. Furthermore, the time required for this transplant greatly affects the comfort of the patient, and is entirely depedent upon the skill of the surgeon, normally requiring approximately 5 minutes by a skilled surgeon.

SUMMARY OF THE INVENTION

Accordingly, it is an object of the present invention to provide a dermatome for cutting thin organic tissue sections for transplanting which overcomes the disadvantages of the prior art.

It is another object of the present invention to provide a dermatome that controls the thickness and width of the tissue sections being cut.

It is a further object of the present invention to provide a dermatome that can reduce the time required for transplanting the organic tissue sections by a skilled surgeon.

It is a still further object of the present invention to provide a dermatome having a support member for positioning the cutting surface of a cutting band relative to the tissue sections, where the support member determines the width and thickness of the cut tissue sections.

It is an added object of the present invention to provide a dermatome as mentioned above having a support which permits the surgeon to select the required width for the tissue sections being cut.

A further object of the present invention is to provide a dermatome as mentioned above wherein the cutting band is removably connected to the support member.

It is a still further object of the present invention to provide a dermatome as mentioned above wherein the cutting band is integrally secured to the support member in a non-removable arrangement.

And yet another added object of the present invention is to provide a dermatome that provides a rapid, simplified, and safe means of cutting thin organic tissue sections for transplanting, one which enables the surgeon to cut tissue sections of proper width and thickness in a simple, quick, and uncomplicated maneuver.

To this end, the present invention relates to a dermatome for cutting thin organic tissue sections for transplanting, the dermatome comprising a thin, resilient cutting band having a cutting surface disposed along a longitudinal edge of the cutting band, a support member for positioning the cutting surface of the cutting band relative to the tissue sections, the support member including holding means for determining width of the cut tissue sections, the holding means maintaining a first portion of the cutting band in a spaced apart relationship to a second portion of the cutting band to provide a loop-like arrangement for the cutting band with the cutting surface extending along the bight portion of the loop-like arrangement, the support member further including guide means for determining thickness of the cut tissue sections, the guide means being disposed between the first and second cutting band sections and spaced a preselected distance from the bight portion, and attachment means provided on the support member to permit the connection of the support member to a handle member. Preferably, the support member includes a head portion and a body portion extending from a central part of the head portion to define a T-shaped arrangement, where the holding means and guide means are provided on the head portion, and the attachment means are provided on the body portion. The cutting band may be removably connected to the support member, or the cutting band may be integrally secured to the support member in a non-removable arrangement.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

DETAILED DESCRIPTION OF THE PREFERRED EMBODIMENTS

Figure 1:
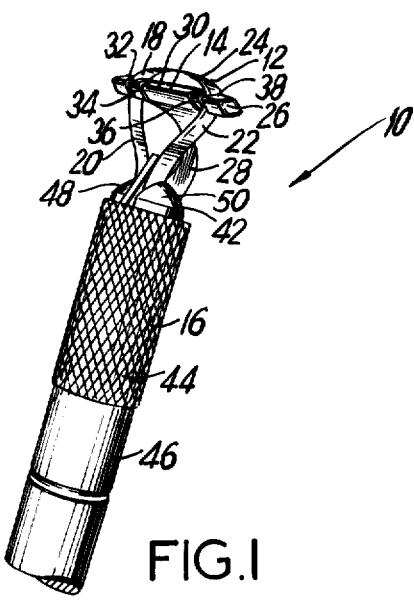
FIG. 1 illustrates a fragmentary perspective view of a dermatome according to the present invention.

Referring now to the drawings, and more specifically to FIG. 1 thereof, the present invention comprises a dermatome generally denoted by the reference character 10. The dermatome is used by a surgeon for cutting thin organic tissue sections for transplanting. The dermatome 10 includes a cutting band or blade 12, a support member 14, and a handle member 16. The cutting band 12 may be fabricated from any suitable metal material capable of providing a sharp cutting surface thereon, such as stainless steel. The support member and the handle member may be fabricated from metal, such as stainless steel, plastic, or any other suitable similar material.

Figure 2:
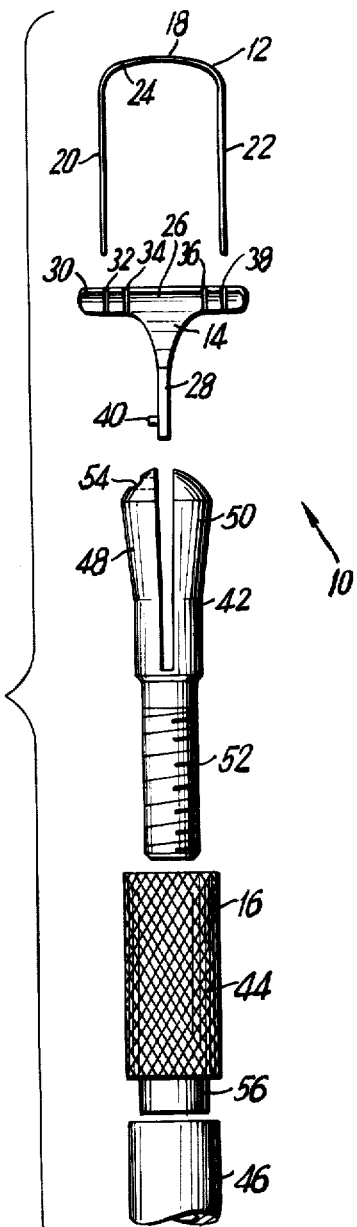
FIG. 2 illustrates a fragmentary, exploded front elevational view of the dermatome.
Figure 3:
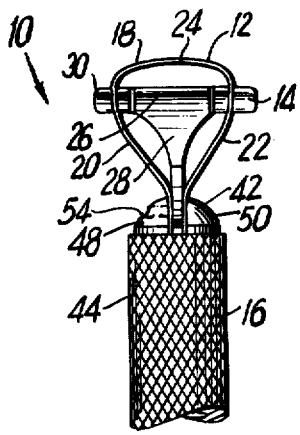
FIG. 3 illustrates a fragmentary, front elevational view of the dermatome shown in FIG. 1.

The cutting band 12 may be preformed in a U-shaped configuration as shown in FIG. 2, or may be a thin flat resilient band capable of being bent into a loop-like arrangement as shown in FIG. 1, where it is understood that the U-shaped band is also resilient and provides a loop-like arrangement. The cutting band 12 includes a bight portion 18 and leg portions 20, 22. A cutting surface 24 extends along a longitudinal edge of the cutting band 12 from the leg 20, along the bight 18, and into the opposite leg 22. It is understood, that the cutting surface 24 need not extend entirely along the edges of the legs 20, 22, where the ends of these legs are disposed within the handle member 16, as will be discussed hereinafter below.

Figure 4:
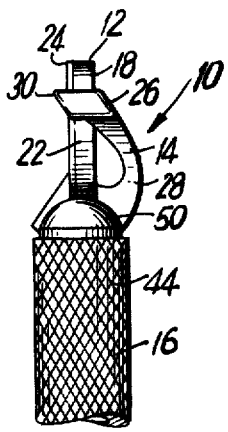
FIG. 4 illustrates a fragmentary side elevational view of the dermatome shown in FIG. 1.

The support member 14 includes a transverse head portion 26 and a body portion 28. The body portion 28 extends from a central part of the head portion 26 to provide a T-shaped configuration. The head portion 16 includes a transversely extending forward edge 30, as best shown in FIG. 4, and two sets of grooves or slots 32, 34 and 36, 38 provided on each side of the body portion 28. The slots 32, 34, 36 and 38 extend perpendicularly through the edge 30 into a substantial portion of the head member 26 to receive the cutting band 12, as will be discussed hereinafter below. Additionally, the body portion 28 is provided with a perpendicularly extending pin member 40, the function of which will also be described below.

The handle member 16 includes a chuck or clamping portion 42, a sleeve portion 44, and an elongated handle portion 46. It is noted, that the end of the handle portion 46 is not shown, where the handle portion 46 may be made in any desired length, such length being considered an obvious matter of choice and design. The chuck 42 includes spaced apart jaws 48 and 50 having tapering outer surfaces thereon, and a threaded shank 52 extending from the jaws. Additionally, the end portion of the jaw 48 is provided with an opening 54 extending transversely therethrough to receive the pin member 40 of the support member 14, as will be described below. The sleeve portion 44 has a knurled outer surface to provide a better grasp thereof, and a collar 56 which is received in the handle portion 46.

To assemble the dermatome 10, the surgeon first decides upon the desired width of the tissue sections, for example, the inner slots 34, 36 will provide a narrower width than the outer slots 32, 38. Accordingly, if the wider width is desired, the surgeon will place the legs 20, 22 in the slots 32, 38 respectively, as shown. The legs 20, 22 will be brought together on opposite sides of the body portion 28 and the bight 18 will be positioned adjacent to the transverse edge 30 for the proper depth of the cut, preferably 0.75 to 1.25mm, to provide the desired thickness of the tissue sections.

At this point, the handle member 16 should be loosely connected together to receive the support member 14 and cutting band 12, where the chuck 42 extends through the sleeve 16 into the handle portion 46 which is internally threaded to receive the threaded shank 52. The handle portion 46 is turned relative to the chuck 42 for the threaded connection therebetween, so that the collar 56 is disposed in the handle portion 46 and a portion of the jaws 48, 50 are disposed within the sleeve 44. The body portion 28 of the support member 14 is now placed between the jaws 48, 50 for attachment thereto, so that the pin member 40 is received in the opening 54 of the jaw 48, and where the legs 20, 22 are also disposed between the jaws 48, 50. The handle portion 46 is now further threadedly turned relative to the chuck 42 to draw the jaws 48, 50 further into the sleeve 44, where the internal surface of the sleeve 44 abuts against the outer tapered surfaces of the jaws 48, 50 to force the jaws 48, 50 towards each other to clamp the body portion 28 of the support member 14 and the leg 20, 22 of the cutting band 12 between the jaws 48, 50.

Before the jaws 48, 50 are fully tightened, the support member 14 may be pivoted about the pin member 40 to any desired angular position relative to the handle member 16. To facilitate the pivoting of the support member 14, the body portion 28 is provided with a curved or arcuate configuration, as best shown in FIG. 4, to permit the surgeon to grasp the support member 14 without interferring with the cutting band 12. Additionally, the lower portion of the body member 28 is enlarged to provide a large or attachment clamping area. After the support member 14 has been positioned at the desired angle, the handle portion 46 is further threadedly turned so that the jaws 48, 50 tightly grip or clamp the support member 14 to prevent any movement thereof relative to the handle member 16.

Thus, the surgeon is now ready to cut the thin tissue sections where the thickness and width of these sections are determined by the dermatome. In cutting the sections, the surgeon rests the transverse edge 30 of the support member 14 against the tissue sections being cut. Accordingly, a skilled surgeon with the aid of the dermatome of the present invention, can reduce the transplanting time from 5 minutes using the scalpel to thirty seconds using the microtome of the present invention. Accordingly, because of the reduced time for transplanting, there is less discomfort for the patient. Furthermore, because the dermatome of the present invention limits the depth of the cut, where excessive depth cutting is eliminated, the patient's pallet heals more quickly. Furthermore, the surgeon is insured of a proper transplant that will effectively adhere to the gum and like parts of the patient.

Figure 5:
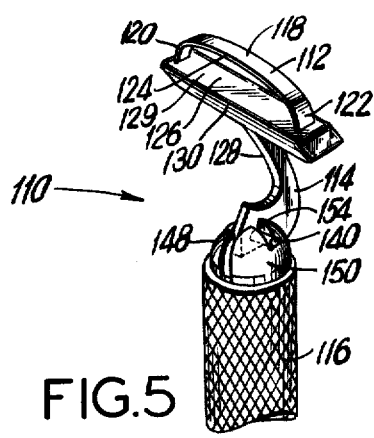
FIG. 5 illustrates a fragmentary perspective view of a modified dermatome according to the present invention.
Figure 6:
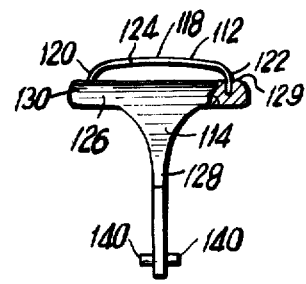
FIG. 6 illustrates a front elevational view, partly in section, of the support member and cutting band of FIG. 5.

FIGS. 5 and 6 disclose a modified dermatome generally denoted by the reference character 110. In this embodiment, the dermatome 110 includes a cutting band or blade 112, a support member 114, and a handle member 116. The above-mentioned dermatome members may be fabricated from any suitable material as mentioned above. As best shown in FIG. 6, the cutting band 112 is integrally secured to the support member 114 in a non-removable arrangement.

The cutting band 112 includes a bight portion 118 and short leg portions 120, 122. A cutting surface 124 extends along a longitudinal edge of the cutting band 112 from the leg 120, along the bight 118, and into the opposite leg 122 in a same manner as mentioned above. The support member 114 holds the cutting band 112 in a loop-like arrangement.

The support member 114 includes a transverse head portion 126 and a body portion 128 similar to the above-mentioned support member 14. The legs 120, 122 of the cutting band 112 are embedded in the upper surface 129 of the head portion 126 adjacent to the transversely extending forward edge 130. Preferably, the cutting band 112 is molded in the support member 114, however, any suitable securing means may be used, such as soddering the legs 120, 122 therein. The body portion 128 of the support member 114 is provided with two oppositely extending pin members 140 to be received in the jaws 148 and 150 of the handle member 116. Accordingly, the jaws 148, 150 are provided with slots 154 to receive the pins 140.

The support member 114 is attached or clamped in the handle member 116 in the same manner as mentioned above, where the pins 140 permit the support member 114 to be pivoted to the desired angular position relative to the handle member 116. It is noted, that the distance between the legs 120, 122 are preselected to provide a predetermined width for the tissue sections being cut. Additionally, the distance between the cutting surface 124 and the transverse edge 130 of the support member 114 is also preselected to provide a predetermined depth of cut or thickness of the tissue sections being cut. Accordingly, a number of different support members 114 and cutting bands 112 secured thereto would be provided to obtain tissue sections varying in thickness and width.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dermatome comprising a thin resilient cutting band provided with a cutting surface disposed along a longitudinal edge of said cutting band, a support member having a transverse head portion for positioning said cutting surface of said cutting band, said head portion including holding means for maintaining a first end of said cutting band in a predetermined spaced apart relationship to a second end of said cutting band to provide a loop-like arrangement for said cutting band with said cutting surface extending along a bight portion of said loop-like arrangement, said predetermined spaced apart relationship determining width of cut, said first and second cutting band ends extending through a surface of said head portion and being disposed within said head portion, said bight portion being spaced from said surface of said head portion in a facing relationship with said surface of said head portion, said support member including guide means for determining depth of cut, said guide means being disposed between said first and second cutting band ends and spaced a preselected distance from said bight portion, and said support member including attachment means to permit connection of said support member to a handle member.

2. A dermatome as claimed in claim 1, wherein said support member includes a body portion, said body portion extending from central part of said head portion to provide a T-shaped arrangement, said first and second end of said cutting band being disposed on opposite sides of said body portion, said guide means being disposed along said head portion, said attachment means being disposed on said body portion.

3. A dermatome as claimed in claim 1, wherein said holding means provide for said cutting band ends being molded in said head portion.

4. A dermatome as claimed in claim 1, wherein said attachment means includes at least one pin element to permit said support member to pivot relative to the handle member to a desired angular position before being fixed to the handle member.

5. A dermatome as claimed in claim 1, wherein said guide means extends outwardly further than said cutting surface to support said dermatome.

6. A dermatome as claimed in claim 1, wherein said holding means integrally secures said cutting band ends to said support member in a non-removable arrangement.

* * * * *